United States Patent [19]
Farivar

[11] Patent Number: 5,250,036
[45] Date of Patent: Oct. 5, 1993

[54] INTRAVENOUS CATHETER PLACEMENT SYSTEM

[76] Inventor: Mohammad Farivar, 307 Hammond St., Chestnut Hill, Mass. 02167

[21] Appl. No.: 980,673

[22] Filed: Nov. 24, 1992

[51] Int. Cl.⁵ .............................................. A61M 5/18
[52] U.S. Cl. ...................................... 604/164; 604/165
[58] Field of Search ............... 604/162, 164, 165, 198, 604/263, 51, 53

[56] References Cited

U.S. PATENT DOCUMENTS

| | | | |
|---|---|---|---|
| 1,213,001 | 1/1917 | Philips | 604/165 |
| 3,406,687 | 10/1968 | Moyer | 128/221 |
| 4,230,123 | 10/1980 | Hawkins, Jr. | 604/165 |
| 4,601,710 | 7/1986 | Moll | 604/165 |
| 4,631,057 | 12/1986 | Mitchell | 604/198 |
| 4,778,453 | 10/1988 | Lopez | 604/110 |
| 4,828,547 | 5/1989 | Sahi | 604/110 |
| 4,931,042 | 6/1990 | Holmes et al. | 604/164 |
| 5,169,387 | 12/1992 | Kronner | 604/164 |

*Primary Examiner*—John D. Yasko
*Assistant Examiner*—Anthony Gutowski
*Attorney, Agent, or Firm*—Pandiscio & Pandiscio

[57] ABSTRACT

An intraveneous catheter placement system is provided which includes an insertion tool/guard assembly and a flexible catheter having an attachment fitting at one of its ends. The insertion device includes a needle and a needle holder. The guard includes an elongate sleeve telescoped over the needle shaft, the sleeve having a blunt distal end and a fitting attached to its proximal end. When assembled, the needle holder, the fitting of the guard and the attachment fitting of the catheter interrelate with one another in mutually telescoping relation such that the needle cannot be removed from the lumen of the catheter prior to the locked deployment of the distal end of the guard sleeve distally of the pointed tip of the needle.

20 Claims, 2 Drawing Sheets

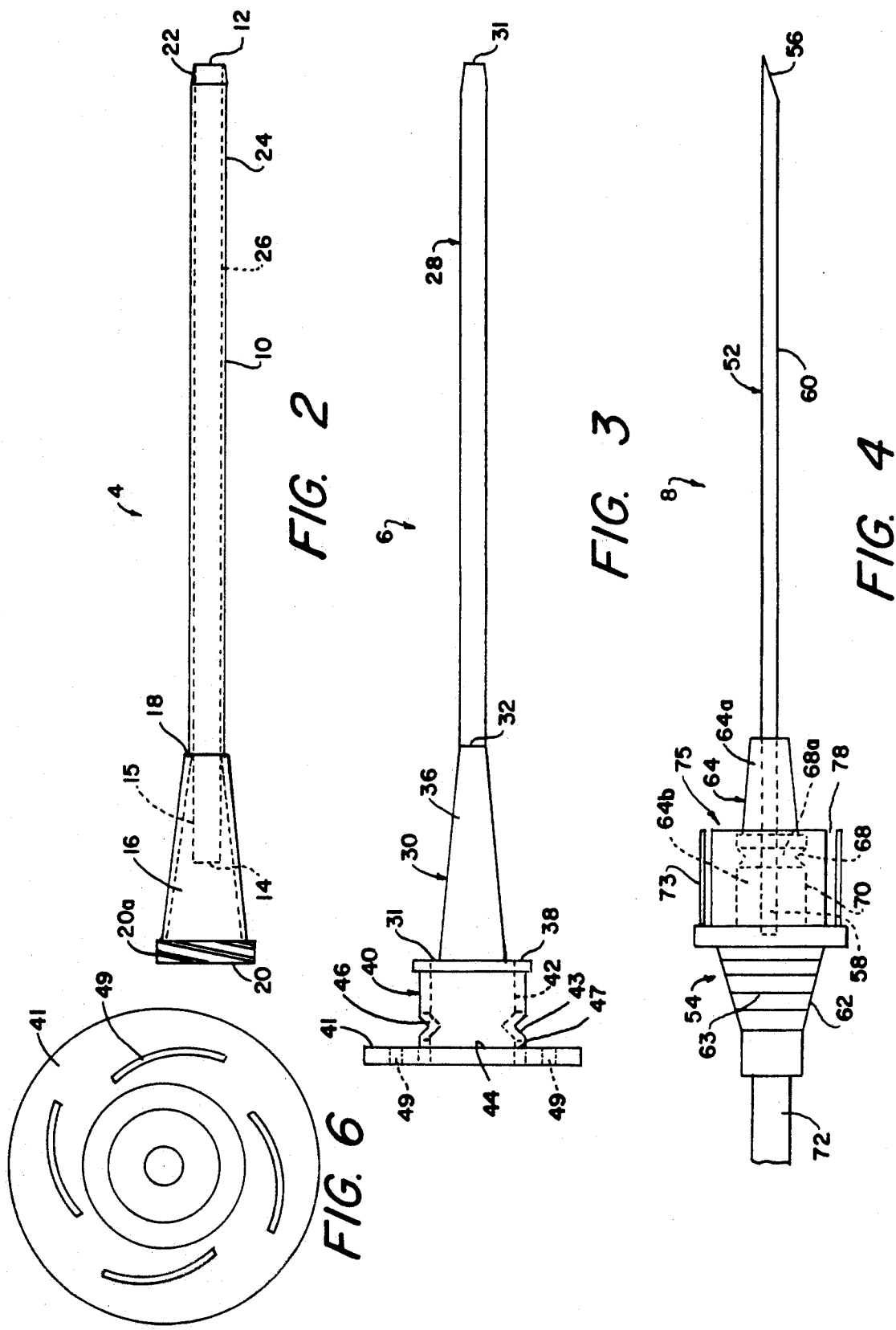

INTRAVENOUS CATHETER PLACEMENT SYSTEM

BACKGROUND

1. Field of Invention

The invention relates generally to medical devices for locating intravenous catheters and the like in a tissue mass. More particularly, the invention relates to an improved system including an insertion device/guard assembly and an intravenous catheter wherein means are provided for ensuring the enclosure of the pointed tip of the tissue piercing means of the insertion device prior to its withdrawal from the lumen of the catheter.

2. Summary of the Prior Art

Modern medical practice routinely includes the injection of medication hypodermically into patients, the positioning of catheters intravenously so as to provide feeding and/or medication introduction passageways through the outer tissue of a patient, and/or the withdrawal of various bodily fluids from patients. In each case, a sharp, unprotected, tissue piercing means such as a needle point is introduced into the caregiving environment. This occurs both (i) prior to the piercing of the patient's skin during the transfer of the needle from its original packaging to the patient, and (ii) subsequent to the withdrawal of the piercing means from the patient during the transfer of the needle to an appropriate disposal facility. The opportunities for the infliction an accidental nick or stick wound to the tissue of the caregiver or others, consequently, are equal to twice the number of tissue piercing procedures performed. It will be understood, therefore, that the accidental piercing of the skin of a health caregiver with any of the various tissue piercing devices commonly utilized by the medical profession is not an uncommon phenomenon. Indeed, it has been estimated that more that 2000 stick type wounds are sustained by health care workers in the United States each day.

A caregiver is subject to accidental needle sticks at all times during which an unenclosed needle point is present in the treatment environment. As a practical matter, this fact presents little danger to the caregiver at the initial stage of most medical procedures because the needle is usually sterile at that time. Once the needle has been placed in contact with the bodily fluids of a patient, however, an accidental needle stick may subject the caregiver to the transmission of serious, or even life threatening, illness. Chief among the diseases which may be communicated in this manner are hepatitis B and the human immunodeficiency virus (HIV). Hepatitis B is serious, but is not necessarily fatal. HIV, on the other hand, eventually causes acquired immune deficiency syndrome (AIDS) which is, so far as is presently known, invariably fatal. The danger arising from needle sticks with a contaminated needle, therefore, represents a severe health risk—a risk which both private institutions and governments worldwide are strenuously endeavoring to reduce.

In response to these health risks, numerous devices have been developed which attempt to remove the tip of a needle from the treatment environment after it has been contaminated by contact with possibly infected blood or other bodily fluids. Generally, these devices provide a member which is movable relative to the pointed end of the needle between a first, so-called "retracted", position wherein the point of the needle is exposed, and a second, so-called "guard", position wherein the point of the needle is effectively removed from the treatment environment. Specifically, in one prior device this has been accomplished by the movement of a shaft within the needle lumen from a retracted position wholly within the needle to a guarding position wherein the distal end of the shaft extends outwardly from within the pointed end of the needle (see, U.S. Pat. No. 4,828,547). Alternatively, an equivalent result has been achieved in other devices by moving a sleeve surrounding the needle shaft from a retracted position wherein the distal end of the sleeve is located proximally of the pointed tip of the needle to a guarding position wherein the distal end of the sleeve is located distally of and enclosing the pointed tip of the needle (see, for example, U.S. Pat. Nos. 4,778,453 and 4,631,056).

To date, the internal shaft alternative is the only one of these mechanisms which has permitted the pointed tip of the needle to be blunted prior to its removal from the tissue mass. Further, sleeves surrounding the needle typically have been provided having diameters substantially in excess of the needle diameter. In some cases this is because locking mechanisms associated with the needle shaft are located internally of the sleeve thereby requiring a large sleeve diameter relative to the needle diameter. In other cases, it has been determined that the danger to the health care worker is reduced by ensuring that the sleeve which must be manipulated by him/her in order to enclose the needle tip is large enough to be easily and securely grasped, yet small enough to prevent access to the needle point by the extremities of a caregiver.

The capability of blunting the needle point prior to its re-entry into the caregiving environment from a location within the body of a patient is very important. So long as the tip of a contaminated needle is exposed in the caregiving environment for any period of time, no matter how small, a finite possibility of the transmission of a fatal disease to a health caregiver is present. Nevertheless, the internal shaft alternative has been found to be excessively complex and expensive. In addition, there remains a finite chance of the infliction of a nick to a health care worker with the point of the needle in that alternative even after the blunting shaft has been deployed in its extended position. This is because in that configuration the point of the needle lies adjacent the outer surface of the blunting shaft such that the needle point remains exposed (albeit substantially flush against the blunting shaft).

Devices for the placement of intravenous catheters and the like in a tissue mass also are well known in the art. Typically, the catheter includes an elongated, hollow, flexible, tube having the smaller end of a generally funnel-shaped connecting fitting attached to one of its ends. The placement device includes a needle holder and a hollow needle. The needle has a pointed distal end and a proximal end connected by a shaft having a length slightly longer than the length of the flexible tube portion of the catheter. The needle holder generally includes a grasping portion and a neck portion. The neck portion surrounds and holds the proximal portion of the needle and has an exterior surface configured to mate with the generally funnel-shaped connecting fitting of the catheter. This configuration allows the fitting to be frictionally held on the neck of the needle holder when the catheter tube is telescoped onto the needle.

In use devices of this type are generally provided in a pre-assembled and presterilized condition such that (i) the catheter resides on the needle with the attachment fitting matingly engaging the neck portion of the needle holder and (ii) the pointed tip of the needle extends distally of the distal end of the catheter tube. The nurse or other caregiver simply takes the device from the package and, while grasping the handle portion of the needle holder, inserts the needle point into the tissue such that it enters a vein of the patient. The needle is then advanced into the vein so as to carry the distal end of the catheter tube (which rides in a close fit to the needle shaft) into the vein. Thereafter, the nurse grasps the attachment fitting on the proximal end of the catheter with one hand and the needle holder with the other hand, and withdraws the needle from the lumen of the catheter while holding the attachment fitting of the catheter stationary with respect to the tissue mass.

The needle then is discarded in a medically and environmentally accepted manner, and a desired source of medication and/or intravenous fluid is attached to the catheter's attachment fitting. In some instances, plastic sheaths are provided for the encasement of the needle prior its being discarded. In other cases, hospital policy may require the caregiver to clip the pointed end off of the shaft of the needle to prevent its subsequent use. As indicated above, however, no means are available whereby the tip of a tissue piercing needle is necessarily enclosed in the normal operation of the device prior to its withdrawal from the patient so as to assure the protection of health care workers from accidental stick wounds.

BRIEF DESCRIPTION OF THE INVENTION

Accordingly, it is the object of this invention to provide an insertion device/guard assembly and intravenous catheter system wherein the pointed tip of the tissue piercing means of the insertion device is necessarily and conveniently enclosed by the guard prior to the piercing means being withdrawable from the lumen of the catheter.

This and other objects of the invention are accomplished in a preferred embodiment by the provision of an insertion device/guard assembly and a flexible catheter. The insertion device/guard assembly includes a needle, a needle holder, and a guard. When assembled, the components of the system interrelate with each other such that the needle cannot be removed from the lumen of the catheter without the prior deployment of the guard over the pointed tip of the needle.

More particularly, the needle is generally hollow and includes a pointed distal end and a proximal end connected by an elongate shaft. The needle holder includes a hollow handle adapted to be grasped by a medical caregiver. The handle is connected to a hollow neck. The neck includes a tapered distal portion surrounding and retaining the shaft of the needle adjacent its proximal end, and a proximal portion connecting the large end of the tapered distal portion to the handle. A passageway extends from the pointed distal end of the needle proximally through the needle and the needle holder. At least one detent extends into the outer surface of the neck adjacent the distal end of the proximal portion thereof. If desired, the detent may take form of a circumferential groove. Further, wall members separated by longitudinal slots extend outwardly from the handle such that the walls together define a socket surrounding the neck. In a preferred embodiment, the socket is a substantially cylindrical, open ended cavity extending outwardly from the handle so as to contain the proximal portion of neck.

The guard includes a sleeve having a blunt distal end and a proximal end. The sleeve has a length slightly shorter than the portion of the shaft of the needle extending from the distal end of the neck. A fitting is attached to the proximal end of the sleeve. That fitting includes a first hollow portion adjacent to the proximal end of the sleeve, a first flange portion extending radially outwardly from the proximal end of the first hollow portion, a second hollow portion centered on the longitudinal axis of the sleeve and extending proximally from the first flange portion, and a second flange portion extending radially outwardly from the proximal end of the second hollow portion.

The first and second hollow portions of the guard are dimensioned to matingly receive the neck. The walls of the second hollow portion also include at least one proximally facing tab having a projection extending radially inwardly therefrom. Each of these projections is sized for reception within the detent in the outer surface of the neck. The tabs also are adapted to flex outwardly relative to the walls of the second hollow portion, so as to thereby allow the projections to ride along the outer surface of the neck proximally of the detent when the neck is fully matingly received within the fitting. The second flange has an outer diameter greater than the outer diameter of the socket, and includes circumferentially spaced curved slots through which the wall members forming the socket extend.

The catheter includes a length of hollow, flexible, biocompatable tubing having a distal end and a proximal end, and an attachment means. The attachment means is generally funnel-shaped, and is attached at its smaller end to the proximal end of the tube. The larger end of the attachment means is dimensioned so as to be capable of matingly engaging the outer surface of the first hollow portion of the fitting of the guard.

The insertion device/guard assembly therefore includes the needle holder/needle assembly and the needle guard telescoped onto the needle shaft. The fitting of the guard matingly engages the neck of the needle holder within the socket portion such that the projections on the ends of the tabs ride along the outer surface of the neck proximally of the detent, and the wall members of the socket extend distally through the slots in the second flange. The assembly of the system is completed by telescoping the catheter onto the guard sleeve carrying needle such that the attachment means releasably, matingly engages the outer surface of the first hollow portion of the fitting of the guard. This engagement also is formed within the volume defined by the socket.

In use, the assembly just described is packaged in a presterilized condition. The caregiver removes the pre-assembled system from the package and removes any outer protective sheath which may cover the exterior of the catheter and the needle point extending therefrom. The needle point is then inserted into the tissue, and thence into a vein of the patient. From this position, the fitting, co-axial guard sleeve and the catheter also enter the vein. Thereafter, the caregiver shifts the axial orientation of the insertion device and the guard relative to each other by sliding the radially outermost portion of the second flange distally along the walls of the socket. This movement forces the guard to move distally relative to the needle holder/needle assembly until the projections on the tabs snap into the detent.

The lengths of the various elements are chosen such that the distal motion of the guard sleeve relative to the needle shaft is such that the distal end of the guard sleeve is moved to a position whereat the pointed end of the needle is enclosed within the guard sleeve when the projections engage the detent. At the same time, the attachment portion of the catheter is moved distally from within the socket to a position along the needle shaft located at a point beyond the distal end of the socket. In this position, the caregiver can grasp exterior of the attachment means and hold it stationary relative to the tissue for the withdrawal of the needle therefrom in the conventional manner. That withdrawal, of course, will be of the needle enclosed within the guard sleeve, rather than of an unprotected needle point as was the case heretofore.

BRIEF DESCRIPTION OF THE DRAWINGS

These and other features and advantages of the present invention will occur to those skilled in the art in view of the following detailed description of a preferred embodiment thereof taken together with the accompanying drawings in which:

FIG. 2 is an illustrative, diagramatic, side view of an I.V. catheter suitable for use in the present invention;

FIG. 3 is an illustrative, diagramatic, side view in partial section of a guard member suitable for use in the present invention;

FIG. 4 is an illustrative, diagramatic, side view in partial section of an insertion device, i.e. a needle/needle holder assembly, suitable for use with the present invention;

FIG. 6 is an illustrative, diagramatic, end view of an alternative guard member in accordance with the invention wherein the socket wall receiving slots curve spirally inwardly relative to the axis of the guard.

DETAILED DESCRIPTION OF PREFERRED EMBODIMENT

Figure 1:
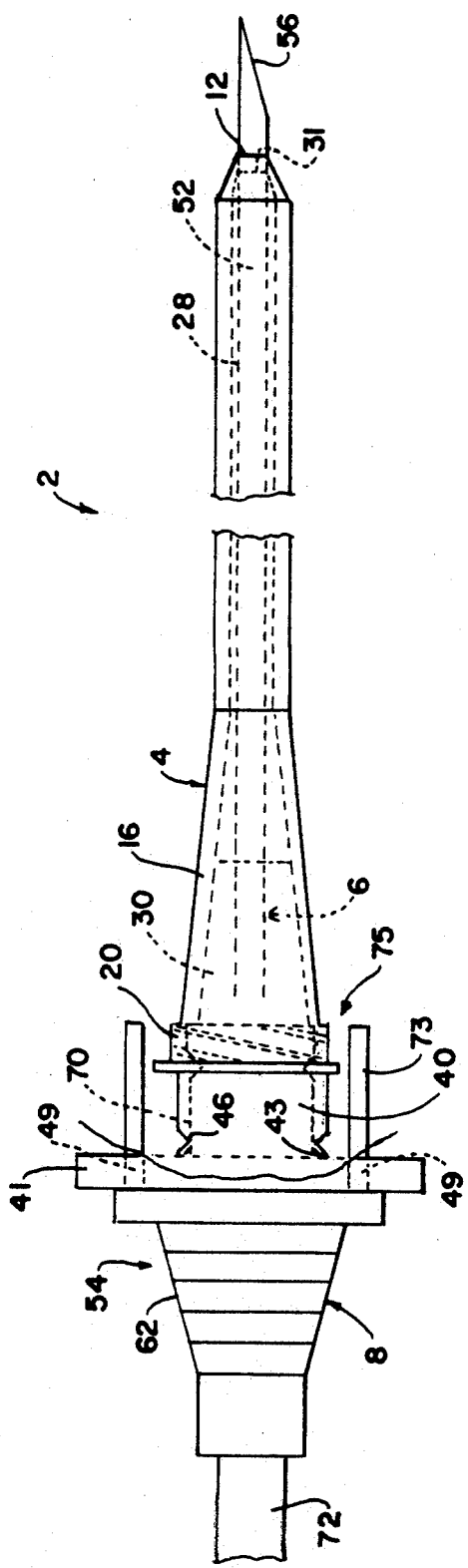
FIG. 1 is an illustrative, diagramatic, side view of an insertion device/guard assembly and intravenous catheter system in accordance with the present invention in its initial, retracted position wherein one of the socket forming walls has been cut away to reveal the relative positions of the other elements of the system.

Referring now to the drawings, and particularly to FIG. 1, there is shown a partially cut away side view of an insertion device/guard assembly and intravenous catheter system 2 in accordance with the present invention. In this figure, the system 2 is shown in its initial, or retracted, position. The system 2 generally includes a catheter, such as I.V. catheter 4 (see FIG. 2), a guard 6 (see FIG. 3) and an insertion device in the form of a needle/needle holder assembly 8 (see FIG. 4).

The catheter 4, best seen in FIG. 2, includes a length 10 of flexible tubing having a first end 12 and a second end 14. Medical grade, biocompatable, plastic tubing is suitable. A rigid, generally funnel-shaped, first attachment fitting 16 is affixed at its smaller end 18 to the second end 14 of the tubing 10 such that a passageway extends from the larger end 20 of the first attachment fitting 16 to the first end 12 of the tubing 10. This affixation is typically accomplished by gluing the second end 14 of the tubing 10 within counterbore 15. The larger end 20 has a ribbed exterior surface 20a to facilitate its grasping by a caregiver.

Conveniently, first attachment fitting 16 may be injection molded of rigid, heat stable, medical grade biocompatable plastic or an equivalent material. Further, the wall 22 of the tubing 10 adjacent first end 12 in the preferred embodiment is pointed, i.e., the wall 22 of the tubing 10 tapers from its outer surface 24 to its inner surface 26 adjacent the end 12 thereof so as to form a "chisel point". The reasons for the shape of the attachment fitting 16 and the "chisel point" on the tubing 10 will become apparent hereinbelow.

The guard 6, best seen in FIG. 3, is preferably formed of rigid, biocompatable material. It includes a tubular portion 28 and a second fitting 30. The tubular portion 28 has a blunt, distal end 31 and a proximal end 32. The second fitting 30, which is centered on the longitudinal axis of the tubular portion 28, includes (i) a first hollow portion 36, (ii) a first flange portion 38 extending radially outwardly from the proximal end 31 of the first hollow portion 38, (iii) a second hollow portion 40 defined by walls 42 extending proximally from the flange portion 38 to a proximalmost edge 44, and (iv) a second flange 41 extending radially outwardly from the proximalmost edge 44 of second hollow portion 40. Wall portion 42 defines at least one proximally facing tab 43 substantially adjacent to proximalmost edge 44. Each such tab 43 is adapted to flex outwardly relative to the adjacent wall, and carries an inwardly extending projection 46 adjacent its outer edge 47. The second flange 41 defines a plurality of circumferentially spaced curved slots 49 adapted to interact with the needle holder as will more fully hereinafter appear.

The needle/needle holder assembly 8, best seen in FIG. 4, includes a needle 52 and a needle holder 54. The needle 52 in the preferred embodiment shown is hollow and made of surgical steel or the like. It includes a pointed distal end 56, a proximal end 58 and an elongated shaft portion 60 extending therebetween. The needle holder 54 includes a hollow handle portion 62 adapted to be grasped by a medical caregiver. The handle 62 is connected to a hollow neck 64 which includes a tapered distal portion 64a surrounding and grasping the proximal portion of the needle shaft. A proximal portion 64b connects the large end of the tapered distal portion 64a to the handle 62 such that a passageway extends from the pointed distal end of the needle through the needle holder. Further, at least one detent 68 extends into the outer surface 70 and the proximal portion 64b of the neck adjacent the distal portion 64a thereof. If desired, the detent 68 may take the form of a groove 68a extending substantially circumferentially around the proximal portion 64b of the neck 64.

The hollow interior of the handle portion 62 of the needle holder 54 connects the open proximal end of the needle 52 to an auxiliary fitting 72 extending outwardly from the handle 62 in a direction different from the direction in which the neck portion 64 extends from the handle portion. Blood flowing through the auxiliary fitting 72 provides a visual indication that the needle is correctly positioned in a vein. The exterior of the handle portion 62, on the other hand, is provided with the desired contour and/or surface for efficient grasping and manipulation of the needle holder by the caregiver. In drawings this is shown as ribbed surface 63. It will be understood, however, that other means of texturing and/or providing a securely graspable surface on the handle may be utilized without departure from the present invention.

Walls 73 extend outwardly from the handle portion 62 in spaced relation to the outer surface 70 of neck portion 64 so as to form a socket 75 therearound which has a depth which is approximately equal to the longitudinal length of the proximal portion 64b of the neck 64. In the particular embodiment shown, the socket 75 is generally cylindrical and is formed by a plurality of wall sections 73 separated by longitudinal slots 78. The importance of this structure will become apparent below.

The above elements are assembled as shown in FIG. 1 to form the insertion device/guard assembly and intravenous catheter system of the present invention. The assembly of that system will now be described followed by a description of the preferred method of using that system for the location of a catheter in a tissue mass without danger of accidental stick or nick wounds by a contaminated needle subsequent to the completion of the location procedure.

In the assembled, first or retracted position, (see, FIG. 1) the tubular portion 28 of the guard 6 is telescoped onto the needle/needle holder combination. More specifically, the tubular portion 28 of the guard 6 extends in a close sliding fit with the needle 52 to a point slightly proximal of the distal tip 56 of the needle 52. The second fitting 30 matingly receives the neck 64 of the needle holder 54 in a close sliding fit such that the projections 46 from the tabs 43 engage the outer surface 70 of the wall 42 adjacent the handle portion 62 of the needle holder 54. At the same time, the wall portions 73 forming the socket 75 extend distally through the curved slots 49 in the second flange 41. The catheter 4 in turn is located in a close sliding fit on the needle/needle holder/guard combination such that the first attachment fitting 16 mates with the outer surface of the first hollow portion 36 of the second fitting 30 and large end 20 of first attachment fitting 16 resides within socket 75. The pointed first end 12 of the catheter 4 engages the needle shaft 60 between the pointed distal end 56 of the needle 52 and the blunt, distal end 31 of tubular portion 28 of the guard 6.

In this configuration, the engagement of the second hollow portion 40 of the second fitting 30 with the outer surface 70 of neck 64 and the ribbed large end 20 of first attachment fitting 16 are both located within the socket 75. This is important because unless one grasps the smooth exterior of the catheter (which is unlikely), the caregiver cannot separate the catheter from the remainder of the assembly in the conventional manner, i.e., by grasping the ribbed portion of the first attachment fitting and withdrawing the needle therefrom. As will be set forth in detail below, the present invention allows the assembly to be manipulated to remove this restraint to the conventional operation of the placement device, but only in a manner which ensures the enclosure of the needle point by the sleeve portion of the guard prior to its withdrawal from the catheter lumen.

It will be understood that typically the system assembly described above will be packaged in a presterilized condition. The caregiver will grasp the handle portion 62 of the needle holder 54, and remove the assembly from the package. Thereafter, the system is manipulated so as to insert the unprotected needle point into the tissue mass such as, for example, into the vein of a patient. Then, the needle 52 is pushed into the tissue so as to carry the distal end of the catheter to the desired depth in the tissue mass. In the normal case, this will entail the movement of the tubular portion 28 of the guard 6 into the tissue as well. Since the flexible catheter tubing preferably covers the blunted distal end 31 of the tubular portion 28 of the guard 6 and includes the "chisel point" described above, however, it is anticipated that this movement will not inflict damage upon the tissue adjacent to the needle entry site.

Once the catheter 4 is appropriately located, the second flange 41 is rotated slightly relative to the needle holder 54 to release any latching engagement between the walls forming the socket 75 and the curved slots 49 in the second flange 41 which may be provided. For example, the slots 49 in the second flange 41 may curve spirally relative to the axis of the tubular portion of the guard such that rotational movement in one direction tends to clamp the second flange and the walls of the socket extending therethough together and rotational movement in the other direction releases this clamping relationship (see, FIG. 6).

Figure 5:
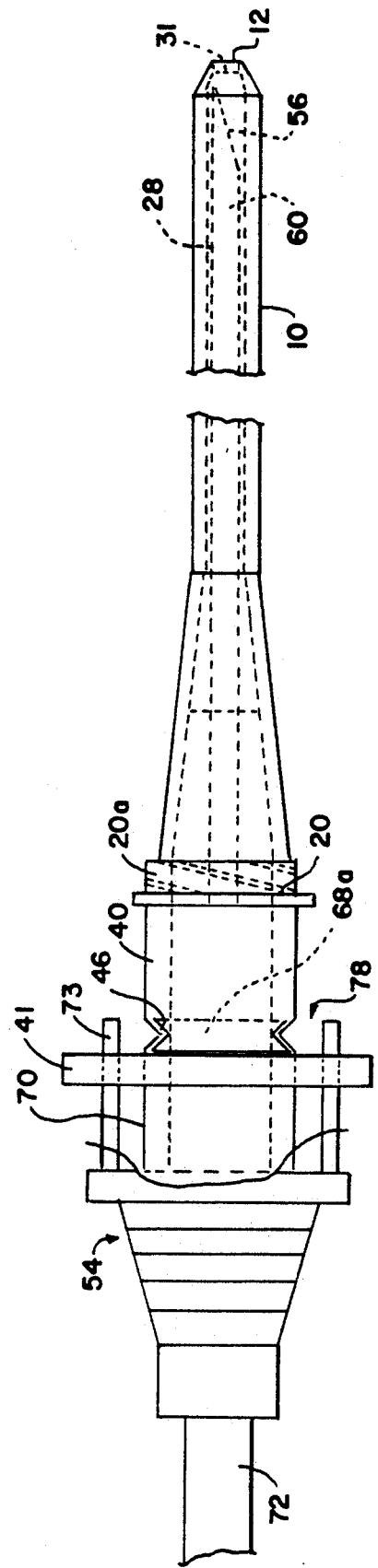
FIG. 5 is an illustrative, diagramatic, side view of the assembly of FIG. 1 similarly cut away to reveal the relative orientations of the system elements in their guarding position.

Thereafter, the second flange 41 is moved distally relative to the needle holder 54 along the slots 78 separating the walls 73 forming the socket 75 until the projections 46 on the tabs 43 snap into the detent 68 in the surface 70 of the proximal neck portion 64a adjacent distal portion 64b (see, FIG. 5). It will be understood that this shift of the guard 6 relative to the needle holder 54 is accomplished while maintaining the needle holder substantially stationary relative to the tissue mass. This shift of orientation accomplishes two distinct objectives.

First, the distal end of the guard sleeve is moved from a retracted position relative to the pointed end of the needle to a position whereat the guard sleeve encloses the pointed end of the needle so as to prevent accidental access thereto by the caregiver. Second, the ribbed proximal end 20 of the attachment means of the catheter is shifted distally beyond the distal end of the socket so as to allow the caregiver to grasp the attachment means for withdrawal of the needle from the lumen of the catheter in the conventional manner. Thus, it will be understood that the needle cannot be withdrawn from the lumen of the catheter until after the guard has been shifted from its retracted to its guard position.

Numerous modifications, variations, changes, alterations, adaptations and the like of the present invention will occur to those skilled in the art in view of the foregoing detailed description of a preferred embodiment thereof. It, therefore, should be understood that the foregoing description is intended as illustrative only, and that the invention is to be understood as being limited only by the terms of the claims appended hereto.

I claim:

1. A self-blunting intravenous catheter insertion system comprising in combination:
   an insertion device/guard assembly and an intravenous catheter removably mountable on said insertion device/guard assembly;
   said insertion device/guard assembly comprising in combination an insertion device comprising:
   (i) a housing,
   (ii) a first attachment fitting and
   (iii) a needle having a shaft, a puncture tip and a blunt end;
   said first attachment fitting including (a) circumferentially spaced first walls extending outwardly from said housing about an axis, said walls terminating at outer edges and together defining a socket having an open end, and (b) a neck portion located centrally of and substantially wholly within said socket, said neck extending outwardly from said housing along an axis and fixedly holding said blunt end of said needle such that said needle shaft extends beyond said open end of said socket along said axis; and a guard member comprising:
 (i) a first sleeve portion, and
 (ii) a second attachment fitting,
said first sleeve portion (a) being sized for close, sliding telescopic engagement with said needle shaft, (b) being slightly shorter than the portion of said needle shaft extending axially from said neck portion and (c) having a blunt distal end and a proximal end; and
said second fitting including (a) a first end and a second end, said first end being attached to said proximal end of said first sleeve portion, (b) a flange extending radially outwardly from said second end of said second fitting, said flange defining slots slidably receiving said first walls therethrough and being axially movable along said first walls between a first position wherein said flange is located substantially adjacent to said housing and a second position wherein said flange is located substantially adjacent to said outer edges of said first walls, the axial distance between said first position and said second position being greater than the difference in length between said first sleeve and the portion of said needle shaft extending outwardly from said neck portion, and (c) second walls extending between said first and second ends of said second fitting, said second walls defining a first open-ended cavity, said second walls being sized to fit at least partially within said socket and said first open-ended cavity being sized to receive said neck portion in close, sliding telescopic engagement therewith when said flange is located in said first position; and said catheter comprising:
 (i) a second sleeve having a third end and a fourth end, said second sleeve being sized to telescopically receive said first sleeve in a close, sliding relationship therewith, and being longer than said first sleeve but shorter than the portion of said needle shaft extending outwardly from said neck portion, and
 (ii) a third fitting attached to said fourth end of said second sleeve, said third fitting including third walls defining a second open-ended cavity adapted to receive said second walls of said second fitting in a close, sliding relationship therewith at least partially within said socket when said catheter is telescopically mounted on said insertion device/guard assembly and said flange is located in said first position.

2. The system of claim 1 wherein said neck portion and said first fitting together define locking means for preventing movement of said second fitting relative to said neck when said flange is located in said second position.

3. The system of claim 2 wherein said neck portion includes an outer surface and a distal end, and wherein said locking means comprises at least one detent in said outer surface of said neck portion located substantially adjacent said distal end of said neck and at least one corresponding inwardly extending projection from said second fitting located substantially adjacent said second end of said second fitting.

4. The system of claim 3 wherein said at least one detent comprises a circumferential groove extending substantially circumferentially about said neck portion.

5. The system of claim 3 wherein each of said projections is mounted on a proximally extending tab portion, each said tab portion being adapted to flex outwardly relative to said first open-ended cavity when said projections bear against said outer surface of said neck portion.

6. The system of claim 1 wherein said slots in said flange curve spirally inwardly relative to said axis such that rotation of said flange in a first direction creates a locking engagement between said flange and said first walls, and rotation of said flange in the other direction releases said locking engagement between said flange and said first walls.

7. The system of claim 1 wherein said needle is made of a substantially rigid, biocompatable metal.

8. The system of claim 1 wherein said guard is made of rigid, biocompatable material.

9. The system of claim 1 wherein said housing is made of rigid material.

10. The system of claim 1 wherein said housing and said neck are hollow and said housing further comprises at least one additional hollow fitting such that a continuous passageway extends from said puncture tip of said needle through said needle shaft, said neck, said housing and said additional fitting.

11. The system of claim 1 wherein said catheter is formed of a flexible, biocompatable material having an inner surface which in its nonstretched condition forms a close, sliding fit with said needle shaft, and defines a chisel edge along the junction of said inner surface and said third end.

12. A method of placing an intravenous catheter or the like comprising the steps of:
 (a) providing a self-blunting intravenous catheter insertion system comprising in combination:
   an insertion device/guard assembly and an intravenous catheter removably mountable on said insertion device/guard assembly;
   said insertion device/guard assembly comprising in combination an insertion device comprising:
    (i) a housing,
    (ii) a first attachment fitting and
    (iii) a needle having a shaft, a puncture tip and a blunt end;
   said first attachment fitting including (a) circumferentially spaced first walls extending outwardly from said housing about an axis, said walls terminating at outer edges and together defining a socket having an open end, and (b) a neck portion located centrally of and substantially wholly within said socket, said neck extending outwardly from said housing along an axis and fixedly holding said blunt end of said needle such that said needle shaft extends beyond said open end of said socket along said axis; and
   a guard member comprising:
    (i) a first sleeve portion, and
    (ii) a second attachment fitting,
   said first sleeve portion (a) being sized for close, sliding telescopic engagement with said needle shaft, (b) being slightly shorter than the portion of said needle shaft extending axially from said neck portion and (c) having a blunt distal end and a proximal end; and said second fitting including (a) a first end and a second end, said first end being attached to said proximal end of said first sleeve portion, (b) a flange extending radially outwardly from said second end of said second fitting, said flange defining slots slidably receiving said first walls therethrough and being axially movable along said first walls between a first position wherein said flange is located substantially adjacent to said housing and a second position wherein said flange is located substantially adjacent to said outer edges of said first walls, the axial distance between said first position and said second position being greater than the difference in length between said first sleeve and the portion of said needle shaft extending outwardly from said neck portion, and (c) second walls extending between said first and second ends of said second fitting, said second walls defining a first open-ended cavity, said second walls being sized to fit at least partially within said socket and said first open-ended cavity being sized to receive said neck portion in close, sliding telescopic engagement therewith when said flange is located in said first position; and said catheter comprising:
(i) a second sleeve having a third end and a fourth end, said second sleeve being sized to telescopically receive said first sleeve in a close, sliding relationship therewith, and being longer than said first sleeve but shorter than the portion of said needle shaft extending outwardly from said neck portion, and
(ii) a third fitting attached to said fourth end of said second sleeve, said third fitting including third walls defining a second open-ended cavity adapted to receive said second walls of said second fitting in a close, sliding relationship therewith at least partially within said socket when said catheter is telescopically mounted on said insertion device/guard assembly and said flange is located in said first position;

(b) mounting said catheter onto said insertion device/guard assembly with said flange thereof located in its first position such that said second open-ended cavity receives said second fitting in a close, sliding relationship therewith at least partially within said socket;

(c) grasping said housing and manipulating said insertion device so as to puncture a tissue mass with said puncture tip of said needle;

(d) then inserting said needle shaft into said tissue so as to locate said third end of said second sleeve of said catheter at a desired location within said tissue mass;

(e) thereafter, while holding said insertion device stationary relative to said tissue mass, sliding said flange distally along said socket from said first position to said second position so as to thereby locate said blunt distal end of said guard sleeve distally beyond said puncture tip of said needle and to locate said third fitting of said catheter distally of the outer edges of said first walls; and (f) thereafter, while holding said third fitting of said catheter stationary relative to said tissue mass, withdrawing said insertion device/guard assembly from said catheter, whereby removal of said insertion device/guard assembly from said catheter can occur only when said puncture tip of said needle is fully enclosed by said blunt end of said guard sleeve.

13. The method of claim 12 wherein said neck portion and said first fitting together define locking means for preventing movement of said second fitting relative to said neck when said flange is located in said second position.

14. The method of claim 13 wherein said neck portion includes an outer surface and a distal end, and wherein said locking means comprises at least one detent in said outer surface of said neck portion located substantially adjacent said distal end of said neck and at least one corresponding inwardly extending projection from said second fitting located substantially adjacent said second end of said second fitting.

15. The method of c)aim 14 wherein said at least one detent comprises a circumferential groove extending about said neck portion.

16. The method of claim 15 wherein each of said projections is mounted on a proximally extending tab portion, each said tab portion being adapted to flex outwardly relative to said first open-ended cavity when said projections bear against said outer surface of said neck portion.

17. The method of claim 13 wherein said slots in said flange curve spirally inwardly relative to said axis such that rotation of said flange in a first direction creates a locking engagement between said flange and said first walls, and rotation of said flange in the other direction releases said locking engagement between said flange and said first walls.

18. The method of claim 13 wherein said needle is made of a substantially rigid, biocompatable metal.

19. The method of claim 13 wherein said guard is made of rigid, biocompatable material.

20. The method of claim 13 wherein said housing and said neck are hollow and said housing further comprises at least one additional hollow fitting such that a continuous passageway extends from said puncture tip of said needle through said needle shaft, said neck, said housing and said additional fitting.

* * * * *